(12) United States Patent
Zeng et al.

(10) Patent No.: US 8,000,937 B2
(45) Date of Patent: *Aug. 16, 2011

(54) METHOD AND APPARATUS FOR WAVEFORM ANALYSIS OF PHYSIOLOGICAL PARAMETERS

(75) Inventors: Lingbo Zeng, Shenzhen (CN); Dazhi Teng, Shenzhen (CN); Saixin Zhou, Shenzhen (CN); Lin Tan, Shenzhen (CN); Qi Wang, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 0 days.

This patent is subject to a terminal disclaimer.

(21) Appl. No.: 12/890,407

(22) Filed: Sep. 24, 2010

(65) Prior Publication Data

US 2011/0015868 A1 Jan. 20, 2011

Related U.S. Application Data

(63) Continuation of application No. 11/965,630, filed on Dec. 27, 2007, now Pat. No. 7,809,528.

(30) Foreign Application Priority Data

Sep. 11, 2007 (CN) .......................... 2007 1 0077037

(51) Int. Cl.
*G01R 13/02* (2006.01)
*G06F 17/40* (2006.01)
(52) U.S. Cl. ........... 702/187; 382/128; 600/523; 702/67
(58) Field of Classification Search ............... 702/19, 702/66, 67, 71, 73, 79, 124, 127, 176, 189; 600/300, 484, 509, 523; 382/128; 705/3
See application file for complete search history.

(56) References Cited

U.S. PATENT DOCUMENTS 5,299,118 A 3/1994 Martens et al.
(Continued)

FOREIGN PATENT DOCUMENTS

CN 1567331 1/2005
(Continued)

OTHER PUBLICATIONS

Office Action mailed Apr. 5, 2010, for U.S. Appl. No. 11/965,630, filed Dec. 27, 1010.
Office Action mailed Oct. 13, 2009, for U.S. Appl. No. 11/965,630, filed Dec. 27, 1010.
(Continued)

*Primary Examiner* — John H Le
(74) *Attorney, Agent, or Firm* — Kory D. Christensen; Stoel Rives LLP

(57) ABSTRACT

A method and an apparatus are provided for performing waveform analysis on physiological parameters. In one embodiment, a method includes reading measurement values of a first physiological parameter relating to time, and displaying them as a trend display graph in a trend display area that includes first coordinates representing time and second coordinates representing the measurement values. The method also includes acquiring a time selected in the trend display graph, and displaying, in a waveform display area, waveform data of a second physiological parameter associated with formation of the first physiological parameter during periods before and after the selected time. The waveform display area includes time coordinates. The disclosed embodiments allow medical staff to view the curve of a patient's physiological parameters throughout a monitoring/therapy period. Medical staff may make a detailed analysis of the waveform data in real time, which may provide a basis for making decisions in the following therapy processes.

36 Claims, 5 Drawing Sheets

U.S. PATENT DOCUMENTS

| | | | |
|---|---|---|---|
| 5,447,164 | A | 9/1995 | Shaya et al. |
| 6,331,159 | B1 | 12/2001 | Amano et al. |
| 7,001,337 | B2 | 2/2006 | Dekker |
| 7,809,528 | B2 * | 10/2010 | Zeng et al. .................... 702/187 |
| 2007/0127793 | A1 | 6/2007 | Beckett et al. |
| 2008/0270188 | A1 | 10/2008 | Garg et al. |

FOREIGN PATENT DOCUMENTS

| | | |
|---|---|---|
| CN | 1756938 | 4/2006 |
| WO | 0070310 | 11/2000 |

OTHER PUBLICATIONS

Notice of Allowance and Fee(s) Due, mailed Jul. 9, 2010, for U.S. Appl. No. 11/965,630, filed Dec. 27, 1010.

Ming-Quan Wang, Yan Han & Feng Yao, Features Analysis of Ultrasonic Inspected Signals, 15 (3) Journal of Test and Measurement Technology 370 (2001) (Chinese).

Li-Wei Huang, Bo-Liang Wang & Xiao-Yang Huang, Implementation of Dynamic Displaying Physiological Information in Real Time in Medical Monitoring System, 41 (6) Journal of Xiamen University (Natural Science) 747 (Nov. 2002) (Chinese).

* cited by examiner

METHOD AND APPARATUS FOR WAVEFORM ANALYSIS OF PHYSIOLOGICAL PARAMETERS

RELATED APPLICATIONS

This application is a continuation of U.S. patent application Ser. No. 11/965,630, filed Dec. 27, 2007, which claims priority to Chinese Patent Application No. 200710077037.4, filed Sep. 11, 2007, both of which are hereby incorporated by reference.

TECHNICAL FIELD

The present disclosure relates to a method and an apparatus for performing waveform analysis of the physiological parameters of patients.

SUMMARY

A method and an apparatus are provided for analyzing a waveform of physiological parameters. Medical staff may clearly review the curve tendencies of a patient's physiological parameters during an entire monitoring/therapy period. By storing and processing the data acquired when monitoring and treating the patient, medical staff may make detailed analyses on the waveform data in real time while viewing the tendencies. Therefore the real-time waveform data may provide a basis for the medical staff to make decisions for ensuing therapy.

DETAILED DESCRIPTION

Figure 1:
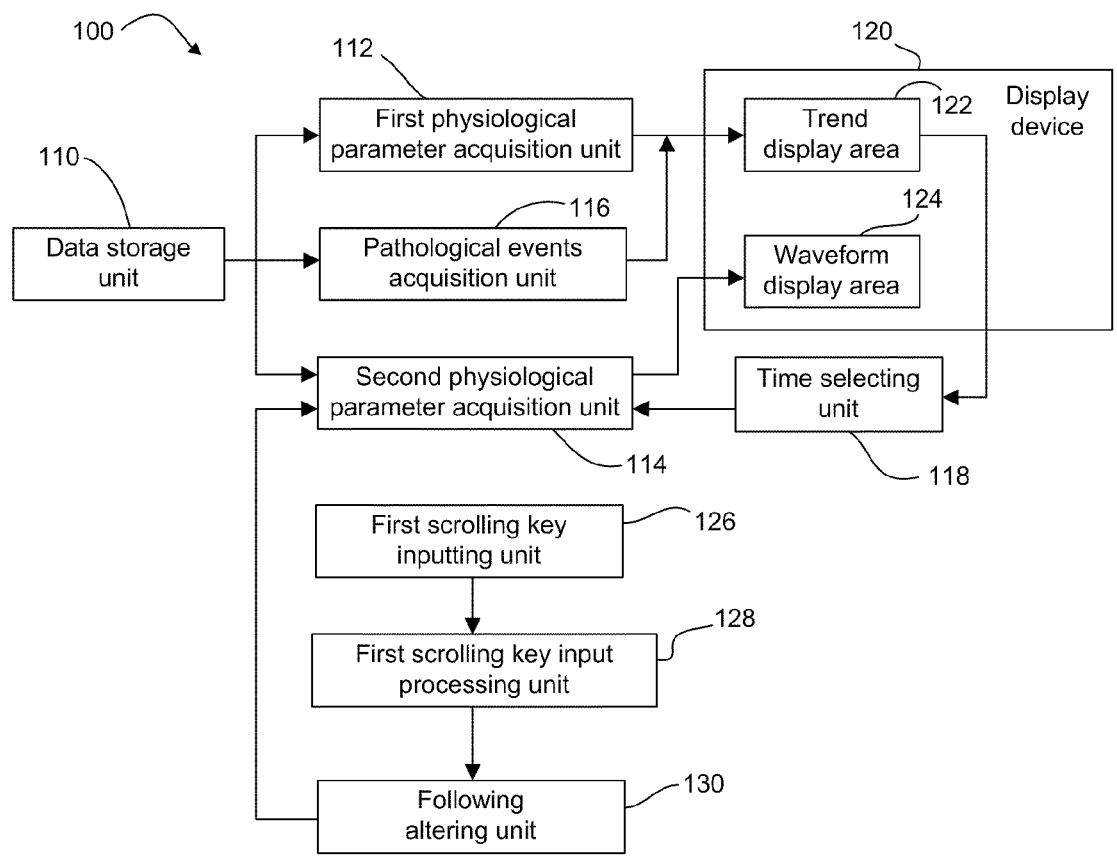
FIG. 1 is a schematic diagram of a waveform analysis apparatus according to one embodiment.

When patients are in critical condition, doctors may apply emergency treatments to the patients that include the use of defibrillator/monitors. A defibrillator/monitor monitors a patient's physiological parameters and stores them during such emergency treatment for a doctor's later analysis to prepare for any ensuing therapy or any later event. However, conventional defibrillator/monitors have disadvantages including the fact that they generally send patient data to other personal computer (PC) terminals for analysis thereon after patient monitoring or therapy occurs. With this approach, however, it is impossible to provide a diagnostic analysis of the pathologic data during a period between therapy procedures, which may delay treatment for the illnesses.

Another disadvantage of conventional defibrillator/monitors is that they generally do not store a sufficient amount of data for diagnosis analysis. For example, while medical staff monitor or treat patients with the defibrillator/monitor, data are generated about the patients (e.g., trend data, waveform data, event data, sound recording data, etc.). During an intermission after the monitoring or therapy, the medical staff can then review and analyze the data stored in the device to prepare for the ensuing therapy or later event. However, because the current defibrillation device can store only some of the data, the medical staff cannot review all of the data, and can hardly make a complete diagnostic analysis on the basis of the pathologic data.

In one embodiment, a method for waveform analysis of physiological parameters includes reading measurement values and corresponding times of a first physiological parameter, and displaying them as a trend display graph in a trend display area of a display device. The trend display area includes first coordinates and a second coordinates that represent the times and the measurement values, respectively. The method also includes acquiring a time selected in the trend display graph, and displaying, in a waveform display area of the display device, waveform data of a second physiological parameter associated with the formation of the first physiological parameter during predetermined periods before and after the selected time. The waveform display area includes time coordinates representing waveform time.

In one embodiment, magnitudes of the measurement values of the first physiological parameter are represented by lengths of respective lines. The method may also include displaying an end-point gauge at an end point of the trend graph. The end-point gauge indicates an end of data corresponding to the first physiological parameter and may be dynamically moved as time elapses.

In one embodiment, acquiring the selected time includes positioning a cursor in the trend display graph at the selected time, receiving the coordinate position of the cursor, and displaying a time corresponding to the coordinate position of the cursor proximate to the cursor in the trend display graph. The method may also include displaying a middle time on the time coordinates of the waveform display area that is a time selected by the cursor. A gauge may also be displayed in the waveform display area for measuring a magnitude of the second physiological parameter.

In one embodiment, inputs are received from a scrolling key in the waveform display area when the waveform display area is in an active state. The method may alter a time on the time coordinates of the waveform display area and the waveform data of the second physiological parameter corresponding to the time. The method may also alter a time on the first coordinates of the trend display graph and a measurement value of the first physiological parameter corresponding to the time in accordance with the altering of the time on the first coordinates of the waveform display area.

In one embodiment, the method also includes displaying a pathologic event identifier at a position corresponding to a time when a pathologic event takes place, and storing the measurement values of the first physiological parameter, the waveform data of the second physiological parameter, pathologic event data, and the time corresponding to when the pathologic event takes place. The method may also include setting the time corresponding to when the pathologic event takes place as a primary key to build an index logic table including data and time so as to associate the data during the storing step.

In one embodiment, the method also includes varying a length of the displayed waveform data of the second physiological parameter in the waveform display area according to a user-selectable wave speed, wherein the faster the wave speed, the shorter a waveform corresponding to the waveform data displayed in the waveform display area.

In one embodiment, the first physiological parameter is a heart rate, and the second physiological parameter is electrocardiogram data. However, those of skill in the art will recognize that other physiological parameters may be analyzed in various embodiments.

An apparatus for waveform analysis of physiological parameters may include a display device configured to display graphs. In one embodiment, the display device includes a trend display area to display measurement values with respect to time of a first physiological parameter. The trend display area includes first coordinates and second coordinates that represent times for measuring the first physiological parameters and the measurement values, respectively. The display device also includes a waveform display area to display waveform data of a second physiological parameter associated with formation of the first physiological parameter. The waveform display area includes time coordinates representing times for measuring the second physiological parameters.

In one embodiment, the apparatus also includes a first physiological parameter acquisition unit to acquire measurement values of the first physiological parameter and the times thereof, and display them on the trend display area. The apparatus may also include a time selecting unit to acquire a selected time in the trend display graph, and a second physiological parameter acquisition unit to acquire waveform data of the second physiological parameter associated with the formation of the first physiological parameter during predetermined periods before and after the selected time thereof, and display them on the waveform display area.

The time selecting unit may include a cursor to select coordinate positions by allowing a user to move and position the cursor, and a cursor monitoring unit to acquire a time corresponding to the cursor's coordinate position while the cursor moves. The apparatus may further include a time display unit to display a time acquired by the cursor monitoring unit in the trend display graph.

In one embodiment, the apparatus further includes a first scrolling key inputting unit to receive inputs of a scrolling key in the waveform display area while the waveform display area is in an active state, a first scrolling key input processing unit to control the second physiological parameter acquisition unit according to the inputs received by the first scrolling key inputting unit so as to alter a time on the time coordinates in the waveform display area and the waveform data of the second physiological parameter corresponding to said time, and a following altering unit to control the first physiological parameter acquisition unit so as to alter a time on the first coordinates in the trend display graph and the measurement value of the first physiological parameter corresponding to said altered time in accordance with the altering of the time at the time coordinates in the waveform display area.

The apparatus may further include a pathologic event data acquisition unit to acquire pathologic event data associated with time, and display a pathologic event identifier at a position corresponding to the time when said pathologic event takes place.

In one embodiment, the apparatus further includes a data storage unit to store the measurement values of the first physiological parameter, the waveform data of the second physiological parameter, the pathologic event data, and the corresponding time when the pathologic event takes place in a storage device, and to set the time as a primary key to build an index logic table including data and time so as to associate the data during the storing.

In another embodiment, a apparatus for waveform analysis of physiological parameters includes first physiological parameter acquisition means for acquiring a measurement value of a first physiological parameter associated with a time that the measurement value is acquired, means for displaying measurement value and corresponding time in a display device's trend display area, time selecting means for acquiring a selected time in the trend display area, a second physiological parameter acquisition means for acquiring waveform data of a second physiological parameter associated with formation of the first physiological parameter during predetermined periods before and after the selected time thereof, and means for displaying waveform data and in a waveform display area of the display device.

Defibrillators or defibrillator/monitors for treating patients according to certain embodiments disclosed herein are provided with high-speed random access memory (RAM) and large-capacity, nonvolatile memory compact flash (CF) cards, which may store a large amount of data. Certain embodiments of the present disclosure use the high-speed memory in the medical device to record real-time trend data of the physiological parameters, the waveform data, and the pathologic events of the patients during monitoring and treatment of patients. At the same time, the patient's trend data, the waveform data, and pathologic events are stored in nonvolatile memory (CF memory card). Thereafter, the pathologic events, the trend data, and the waveform data are shown in graphics by associating the same and taking the generating time of the data as a handle. The medical staff can then make quick diagnoses on patients.

With the systems and methods of the present disclosure, the medical staff can see the curve trend of a patient's physiological parameters clearly on the medical instruments in real time throughout the monitoring/therapy periods. Moreover, they can make a detailed analysis of the waveform data in real time, thus providing a basis for making decisions in the ensuing therapy.

In one embodiment, the defibrillator/monitor has a clinical mode and a nonclinical mode. The clinical mode refers to an operation mode in which a patient may be monitored and treated. In one configuration, the clinical mode is mainly provided for professional medical staff. The clinical mode includes a monitoring mode, a pacing mode, a manual defibrillation mode, and an automated external defibrillator (AED) mode. The nonclinical mode refers generally to an operation mode in which the device manages and maintains the patient's data. In the nonclinical mode, the patient cannot be monitored and treated using the device. The nonclinical mode includes a configuration mode, a self-examination mode, a files management mode, a user maintenance mode, a manufacturer maintenance mode, and a demo mode.

FIG. 1 shows a waveform analysis apparatus 100 for measuring and analyzing a patient's physiological parameters, which includes a data storage unit 110, a first physiological parameter acquisition unit 112, a second physiological parameter acquisition unit 114, a pathologic events acquisition unit 116, and a time selecting unit 118. The first physiological parameter acquisition unit 112, second physiological parameter acquisition unit 114, and pathologic events acquisition unit 116 acquire respective data associated with time from the data storage unit 110, and have these data and their corresponding times displayed on a display area of a display device 120. The display device 120 has a trend display area 122 and a waveform display area 124. The trend display area 122 includes horizontal coordinates and longitudinal coordinates, which represent time and measurement values respectively. The trend display area 122 is used to display measurement values of the first physiological parameter associated with time. The time of the horizontal coordinates is the time for measuring the first physiological parameter. The pathologic events acquisition unit 116 displays a pathologic event identifier at a position corresponding to the time when this pathologic event takes place in the trend display graph. The waveform display area 124 includes time coordinates that represent time, and is used to display the waveform data of the second physiological parameter associated with the forming of the first physiological parameter. The time on the time coordinates is the time for measuring the waveform data of the second physiological parameter.

The waveform analysis apparatus 100 may further comprise a first scrolling key inputting unit 126, a first scrolling key input processing unit 128, and a following altering unit 130. The first scrolling key inputting unit 126 is used to receive inputs from a scrolling key in the waveform display area 124 when the waveform display area 124 is in an active state. The first scrolling key input processing unit 128 is used to control the second physiological parameter acquisition unit 114 according to the inputs received by the first scrolling key inputting unit 126, so as to alter a time at the time coordinates in the waveform display area 124 and the waveform data of the second physiological parameter corresponding to said time.

The following altering unit 130 is used to control the first physiological parameter acquisition unit 112 so as to alter the time at the horizontal coordinates and the measurement value of the first physiological parameter corresponding to said time in the trend display graph, by following the altering of the time at the time coordinates in the waveform display area 124.

The waveform analysis apparatus 100 may further comprise a second scrolling key inputting unit (not shown) and a second scrolling key input processing unit (not shown). The second scrolling key inputting unit is used to receive inputs from a scrolling key in the trend display area 122 when the trend display area 122 is in an active state. The second scrolling key input processing unit is used to control the first physiological parameter acquisition unit according to the inputs received by the second scrolling key inputting unit, so as to alter the time at the horizontal coordinates and the measurement value of the first physiological parameter corresponding to said time in the waveform display area 124.

Although not shown in FIG. 1, the data storage unit 110 includes a high-speed RAM and a CF card for storing patient data.

Figure 2:
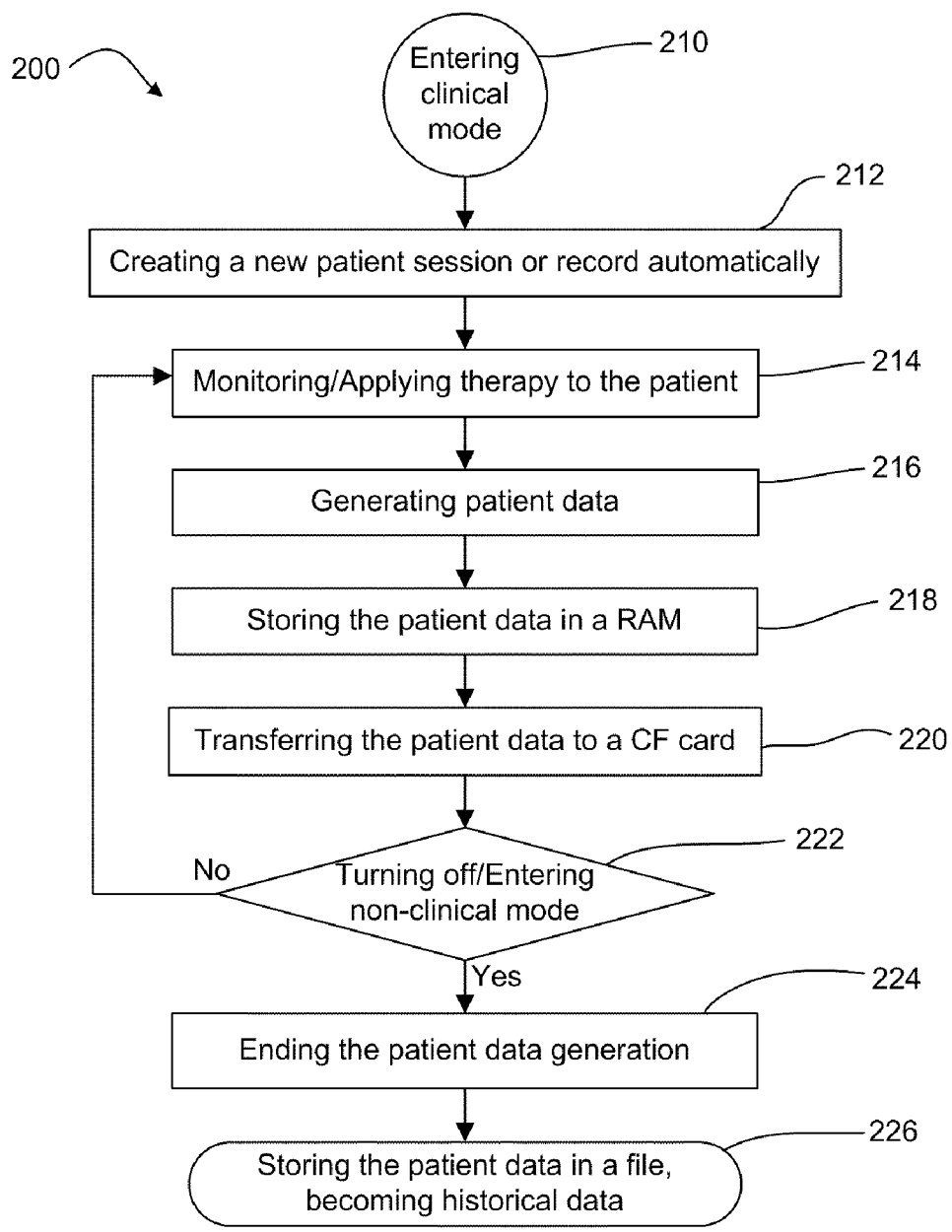
FIG. 2 is a flowchart of a data generating process according to one embodiment.

FIG. 2 shows a process 200 for generating the patient data according to one embodiment. When a defibrillator/monitor enters 210 the clinical mode (e.g., enters when powering on or switching from nonclinical mode), it automatically creates 212 a new patient session or record in one embodiment. A series of data generated during the subsequent monitoring/therapy 214 of the patient is recorded automatically in relation to the current patient's name or other identifier. The data generated 216 during the processes of monitoring/therapy are stored 218 in the RAM of the defibrillator/monitor in real time. The system transfers 220 the data in the RAM to the CF card in the defibrillator/monitor at a predetermined time interval (such as 10 seconds), repeatedly. Therefore, in one embodiment, the patient data are generated and stored in the CF card continuously.

During the monitoring/therapy of the patient, the apparatus may be powered off or may enter 222 into the nonclinical mode. Thereafter, the storage of the patient data is automatically stopped 224, and the current patient data are stored 226 in the archives to form a new historical patient record. Thus, in one embodiment, the data of the patient is terminated immediately when powering off or when entering into the nonclinical mode is finished.

Figure 3:
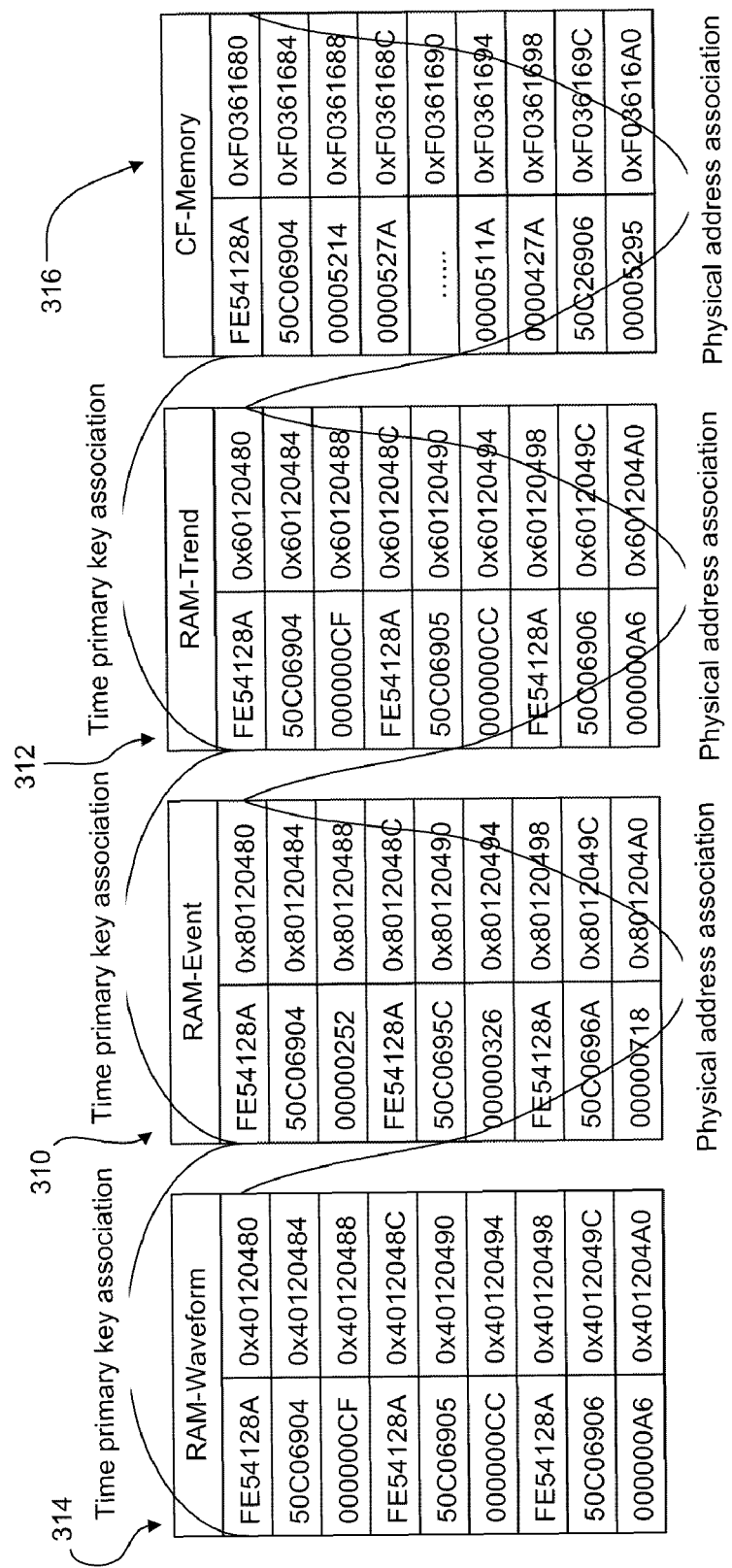
FIG. 3 is a schematic diagram of data associations according to one embodiment.

As a result, the data generated during monitoring/therapy by the defibrillator/monitor are stored in the memory of the defibrillator/monitor. As shown in FIG. 3, these data are stored generally under three categories, which are pathological event data 310, trend data 312, and waveform data 314.

In one embodiment, when the patient data are generated, the main system processing unit (CPU) of the apparatus stores the contents of the data and the data generating time (e.g., in seconds) in the system memory unit. Thereafter, the system periodically stores the patient data and the time in a nonvolatile memory device (e.g., CF-Memory 316 shown in FIG. 3), and generates a time identifier. During the storing, a data index logic table is built to associate the data by setting the time as a primary key.

During intermissions of the monitoring and/or therapy, the medical staff may enter the waveform analysis interface through a system menu to make a pathologic analysis on patient's holographic waveforms.

Figure 4:
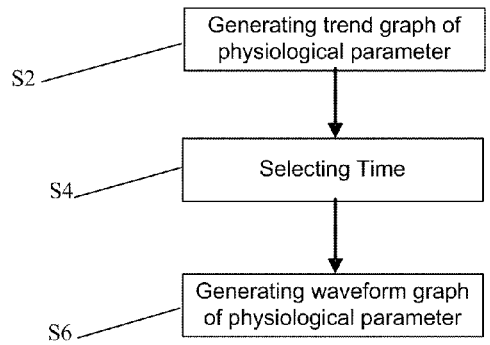
FIG. 4 is a flowchart of a waveform analysis method according to one embodiment.

FIG. 4 shows a flowchart of a method for waveform analysis. Referring to FIGS. 1 and 4, at step S2, the first physiological parameter acquisition unit 112 acquires measurement values of the first physiological parameter associated with time, and displays them on a trend display area 122 comprising horizontal coordinates and longitudinal coordinates, which represent time and measurement values, respectively, on a display device. The time at the horizontal coordinates in the trend display area 122 is a time for measuring the first physiological parameter. At the same time, the pathologic event acquisition unit 116 displays a pathologic event identifier at a position corresponding to the time of the pathologic event in the trend display graph. Thereafter, the method proceeds to step S4.

At step S4, the time selecting unit 118 acquires the time selected in the trend display graph. Although not shown, the time selecting unit 118 comprises a cursor, a cursor monitoring unit, and a time display unit. The cursor is moved in the trend display area 122. The cursor monitoring unit can acquire the time corresponding to the cursor's coordinate position as the cursor is moving. The time display unit displays the time acquired by the cursor monitoring unit in the vicinity of the cursor identifier (e.g., behind the cursor) inside the trend display graph. The cursor monitoring unit acquires the time corresponding to this position as a selecting time by making the cursor stay stationary for a period of time (e.g., two seconds) or clicking to select a certain position. Thereafter, the method proceeds to step S6.

At step S6, the second physiological parameter acquisition unit 114 acquires the waveform data of the second physiological parameter, which are associated with the formation of the first physiological parameter, in the periods before and after the selected time. Moreover, it displays these data in the waveform display area 124 on the display device 120, which includes time coordinates, such that the time at the time coordinates in the waveform display area 124 is the time for measuring the waveform data of the second physiological parameter.

Figure 5:
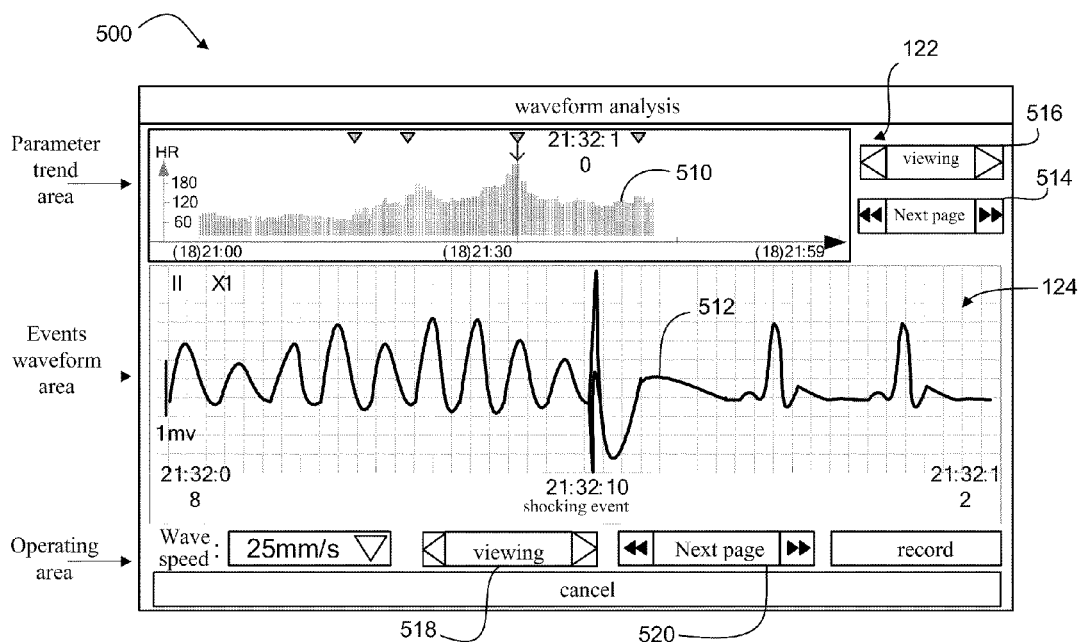
FIG. 5 is a schematic diagram of a waveform analysis interface according to one embodiment.

The waveform analysis graph created by the above steps is shown as FIG. 5. In one embodiment, the waveform analysis interface 500 is divided into two main portions: the upper portion is the trend display area 122 of physiological parameters, and the lower portion is the waveform display area 124 of physiological waveforms. However, in alternative embodiments, the lower portion may be the trend display area 122 of physiological parameters, while the upper portion is the waveform display area 124 of physiological waveforms. The trend display area 122 shows a patient's physiological parameter trend graph 510 and identifies the pathologic events. The waveform display area 124 shows a patient's holographic waveforms 512 during monitoring and/or therapy. The positions of the trend display area 122 and waveform display area 124 are interchangeable.

The trend display area 122 and the waveform display area 124 are described in detail below.

Figure 6:
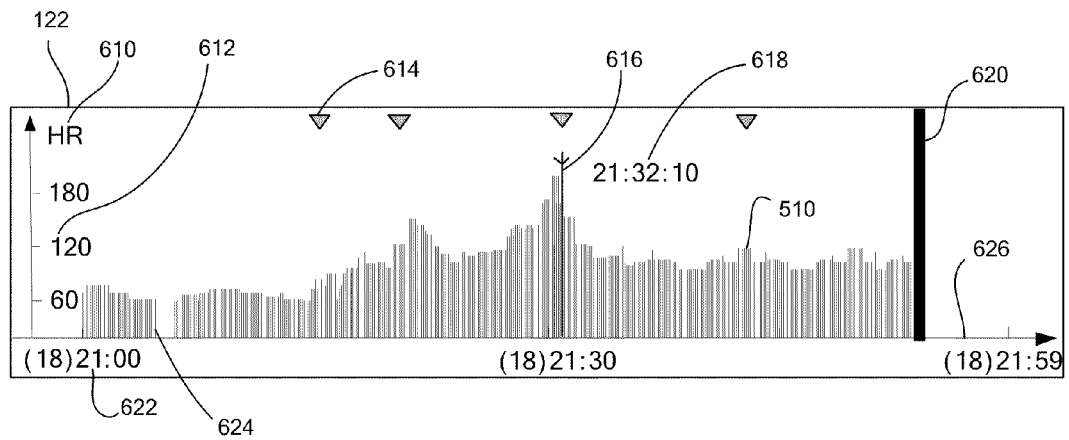
FIG. 6 is a schematic diagram of a trend display area according to one embodiment.

FIG. 6 is a schematic diagram displaying the trend display area 122, which includes a name 610 of a physiological parameter (e.g., heart rate (HR)), parameter coordinates 612 (e.g., beats per minute), event icons 614 (four shown), a positioning cursor 616, a cursor time 618, an end-point gauge 620, a time scale 622, and an area without data 624.

Several (e.g., five) scales are shown on a time coordinate axis 626, which divide the time coordinate axis 626 into four parts equally. Each part indicates 15 minutes, i.e., there are 60 minutes total. There are three time scales 622 under the time coordinate axis 626. They are located at the left, middle, and right of the axis 626. The time scales are displayed such that they descend from the right side to the left side. A next page of the graph 510 may be displayed by operating a "next paging" key (see, e.g., the "next page" key 514 in FIG. 5) in the trend area 122 so as to review trend graphs 510 of other time periods.

The name 610 of the first physiological parameter, such as HR (heart rate), is shown on the top of the parameter coordinate axis 612. Alternatively, the first physiological parameter may also be set as, for example, ST, blood oxygen saturation, or heart pulse cycle. The parameter coordinates 612 indicate three scales from the top side to bottom side. The values of the parameters are displayed in a descending sequence from the top side to the bottom side.

A positioning cursor 616 is provided in the trend display area 122 to position a specific time point for conveniently reviewing the trend and waveforms in the waveform display area 124. After a "scrolling" key (see, e.g., the view key 516 in FIG. 5) in the trend display area 122 is pressed, the positioning cursor 616 can be moved by scrolling a rotary encoder. The time 618 of the cursor's current position is shown behind the positioning cursor in real time. If the positioning cursor 616 has been positioned at a specific time point over a certain period of time (e.g., one second or two seconds), the waveform data in the waveform display area 124 are refreshed dynamically to display the physiological parameter waveforms 512 within several seconds before and after this time point (in one embodiment it is set as two seconds at default, and the length of the waveforms 512 can be changed by selecting the speed of the waveforms 512).

On the top of the trend graph 510, the events are labeled with the event icons 614 (e.g., triangle icons). These event icons 614 indicate that corresponding pathologic events have taken place at these time points (such as drug applying events, physiological alarming events, shocking events, etc.).

The trend graph 510 is composed of several vertical lines, each of which represents a time point, and the length of each line (in this example embodiment) represents the patient's HR value at this time point. The HR value may also be represented by a dot. In such an embodiment, the longitudinal coordinate of the dot represents the HR value.

In the trend graph 510, the blank area 624 indicates that there are no effective physiological parameter measurement values during the period of time corresponding to the area 624.

The trend graph 510 provides a real-time refreshing function, and the trend graph 510 is thereby refreshed dynamically as time elapses.

At the end of the trend data, the end-point gauge 620 is identified to indicate that the patient's trend data ends at this time point. The end-point gauge 620 moves to the right dynamically as the time elapses (e.g., a dynamically refreshing function of the trend data).

Figure 7:
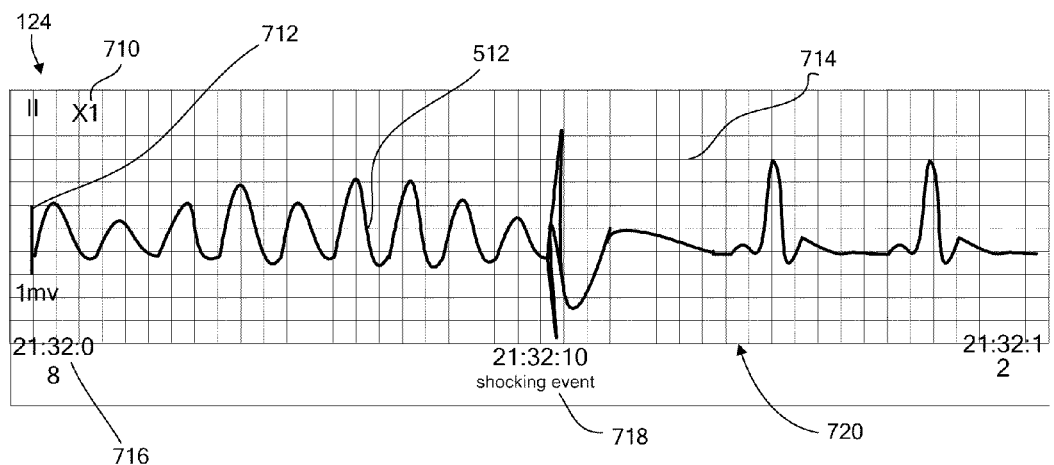
FIG. 7 is a schematic diagram of a waveform display area according to one embodiment.

FIG. 7 is a schematic diagram of a waveform display area 124, which includes a waveform name and gain 710, 22 a waveform dimension 712, the waveform 512 of the second physiological parameter, a grid 714, a time scale 716, and an event name 718.

In one embodiment, the waveform display area 124 includes three time scales 716 labeled below a time coordinate axis 720; one is located at the left, one is located in the middle, and one is located at the right. The time coordinate in the middle of the waveform display area 124 is the time for the positioning cursor 616 of the trend display area 122. The time scales 716 are displayed in a descending sequence from right to left.

The time scales vary in accordance with the wave speed. That is, the faster the wave speed is, the shorter the waveform is, for example:

1) When the wave speed is 6.25 mm/s, there are 17 scales displayed on the time coordinate axis 720, which divide the time coordinate axis 720 into 16 parts equally. Each part indicates one second; that is, there are 16 seconds total.

2) When the wave speed is 12.5 mm/s, there are nine scales displayed on the time coordinate axis 720, which divide the time coordinate axis 720 into eight parts equally. Each part indicates one second; that is, there are eight seconds total.

3) When the wave speed is 25 mm/s, there are five scales displayed on the time coordinate axis 720, which divide the time coordinate axis 720 into four parts equally. Each part indicates one second; that is, there are four seconds total.

4) When the wave speed is 50 mm/s, there are three scales displayed on the time coordinate axis 720, which divide the time coordinate axis 720 into two parts equally. Each part indicates one second; that is, there are two seconds total.

The waveforms 512 at other time points can be reviewed using a "scrolling" key (e.g., see the "viewing" key 518 in FIG. 5) and a "next page" key (e.g., see the "next page" key in FIG. 5).

The second physiological parameter may be, for example, an ECG (electrocardiogram) parameter. In such an embodiment, the ECG gauge 712 is displayed in the waveform display area 124 to measure a magnitude of the ECG waveform 512.

In one embodiment, the physiological parameter waveform 512 may be zoomed in or out by selecting different wave speeds. The waveform information may contain the waveform names and gains 710, and wave filtering modes. It may be displayed at the top left corner of the waveform area 124 in one implementation.

The waveform area 124 may be provided with a grid 714 to measure the length of the waveform 512 and determine the form of the waveform 512, for example, ST diagnostics.

The pathologic event name 718 may be displayed below the time scale 716 of the waveform area 124 to indicate that a pathologic event takes place at this time. The above-mentioned time may also be provided on the longitudinal coordinates, and the measurement value may also be provided at the horizontal coordinates.

Detailed descriptions of several example embodiments are provided above. However, the invention is not restricted to these example embodiments. Without departing from the scope of the invention, those skilled in this art may make changes and modifications, which will all fall into the claims of the invention.

Furthermore, the described features, operations, or characteristics may be combined in any suitable manner in one or more embodiments. It will also be readily understood that the order of the steps or actions of the methods described in connection with the embodiments disclosed may be changed as would be apparent to those skilled in the art. Thus, any order in the drawings or Detailed Description is for illustrative purposes only and is not meant to imply a required order, unless specified to require an order.

Embodiments may include various steps, which may be embodied in machine-executable instructions to be executed by a general-purpose or special-purpose computer (or other electronic device). Alternatively, the steps may be performed by hardware components that include specific logic for performing the steps or by a combination of hardware, software, and/or firmware.

Embodiments may also be provided as a computer program product including a machine-readable medium having stored thereon instructions that may be used to program a computer (or other electronic device) to perform processes described herein. The machine-readable medium may include, but is not limited to, hard drives, floppy diskettes, optical disks, CD-ROMs, DVD-ROMs, ROMs, RAMs, EPROMs, EEPROMs, magnetic or optical cards, solid-state memory devices, or other types of media/machine-readable medium suitable for storing electronic instructions.

As used herein, a software module or component may include any type of computer instruction or computer executable code located within a memory device and/or transmitted as electronic signals over a system bus or wired or wireless network. A software module may, for instance, comprise one or more physical or logical blocks of computer instructions, which may be organized as a routine, program, object, component, data structure, etc., that performs one or more tasks or implements particular abstract data types.

In certain embodiments, a particular software module may comprise disparate instructions stored in different locations of a memory device, which together implement the described functionality of the module. Indeed, a module may comprise a single instruction or many instructions, and may be distributed over several different code segments, among different programs, and across several memory devices. Some embodiments may be practiced in a distributed computing environment where tasks are performed by a remote processing device linked through a communications network. In a distributed computing environment, software modules may be located in local and/or remote memory storage devices. In addition, data being tied or rendered together in a database record may be resident in the same memory device, or across several memory devices, and may be linked together in fields of a record in a database across a network.

It will be understood by those having skill in the art that many changes may be made to the details of the above-described embodiments without departing from the underlying principles of the invention. The scope of the present invention should, therefore, be determined only by the following claims.

What is claimed is:

1. A method used in an apparatus for waveform analysis of physiological parameters, the apparatus including a physiological parameter acquisition unit and a display device, the method comprising:
   reading, using the physiological parameter acquisition unit, measurement values and corresponding times of a first physiological parameter, and displaying a plurality of variations in the measurement values of the first physiological parameter over time as a trend display graph in a trend display area of the display device, the trend display area comprising a first coordinate and a second coordinate that represent the times and the measurement values, respectively, wherein displaying the plurality of variations in the measurement values with respect to the second coordinate in the trend display area indicates a trend in the first physiological parameter throughout a monitoring period;
   acquiring a time selected in the trend display graph; and
   displaying, in a waveform display area of the display device, waveform data of a second physiological parameter associated with the formation of the first physiological parameter during predetermined periods before and after the selected time, the waveform display area comprising time coordinates representing waveform time.

2. The method according to claim 1, wherein magnitudes of the measurement values of the first physiological parameter are represented by lengths of respective lines.

3. The method according to claim 2, further comprising:
   displaying an end-point gauge at an end point of the trend graph, the end-point gauge indicating an end of data corresponding to the first physiological parameter; and
   moving the end-point gauge dynamically as time elapses.

4. The method according to claim 1, wherein acquiring the selected time comprises:
   positioning a cursor in the trend display graph at the selected time.

5. The method according to claim 4, further comprising:
   receiving the coordinate position of the cursor; and
   displaying a time corresponding to the coordinate position of the cursor proximate to the cursor in the trend display graph.

6. The method according to claim 4, further comprising:
   displaying a middle time on the time coordinates of the waveform display area, wherein the middle time is the time selected by the cursor.

7. The method according to claim 6, further comprising:
   displaying a gauge in the waveform display area for measuring a magnitude of the second physiological parameter.

8. The method according to claim 6, further comprising:
   receiving inputs from a scrolling key in the waveform display area when the waveform display area is in an active state;
   altering a time on the time coordinates of the waveform display area and the waveform data of the second physiological parameter corresponding to the time; and
   altering a time on the first coordinates of the trend display graph and a measurement value of the first physiological parameter corresponding to the time in accordance with the altering of the time on the first coordinates of the waveform display area.

9. The method according to claim 8, further comprising:
   displaying a pathologic event identifier at a position corresponding to a time when a pathologic event takes place.

10. The method according to claim 9, further comprising:
    storing the measurement values of the first physiological parameter, the waveform data of the second physiological parameter, pathologic event data, and the time corresponding to when the pathologic event takes place, in a data storage device; and setting the time corresponding to when the pathologic event takes place as a primary key to build an index logic table including data and time so as to associate the data during the storing step.

11. The method according to claim 8, further comprising: varying a length of the displayed waveform data of the second physiological parameter in the waveform display area according to a user-selectable wave speed, wherein the faster the wave speed, the shorter a waveform corresponding to the waveform data displayed in the waveform display area.

12. The method according to claim 1, wherein the first physiological parameter is a heart rate, and the second physiological parameter is electrocardiogram data.

13. An apparatus for waveform analysis of physiological parameters, comprising:
   a display device configured to display graphs, the display device comprising:
      a trend display area to display a plurality of variations in measurement values with respect to time of a first physiological parameter, wherein the trend display area comprises first coordinates and second coordinates that represent times for measuring the first physiological parameters and the measurement values, respectively, and, wherein displaying the plurality of variations in the measurement values with respect to the second coordinate in the trend display area indicates a trend in the first physiological parameter throughout a monitoring period; and
      a waveform display area to display waveform data of a second physiological parameter associated with formation of the first physiological parameter, the waveform display area comprising time coordinates representing times for measuring the second physiological parameters.

14. The apparatus according to claim 13, further comprising:
   a first physiological parameter acquisition unit to acquire measurement values of the first physiological parameter and the times thereof, and display them on the trend display area;
   a time selecting unit to acquire a selected time in the trend display graph; and
   a second physiological parameter acquisition unit to acquire waveform data of the second physiological parameter associated with the formation of the first physiological parameter during predetermined periods before and after the selected time thereof, and display them on the waveform display area.

15. The apparatus according to claim 14, wherein the time selecting unit comprises:
   a cursor to select coordinate positions by allowing a user to move and position the cursor; and
   a cursor monitoring unit to acquire a time corresponding to the cursor's coordinate position while the cursor moves.

16. The apparatus according to claim 15, further comprising:
   a time display unit to display a time acquired by the cursor monitoring unit in the trend display graph.

17. The apparatus according to claim 13, further comprising:
   a first scrolling key inputting unit to receive inputs of a scrolling key in the waveform display area while the waveform display area is in an active state;
   a first scrolling key input processing unit to control the second physiological parameter acquisition unit according to the inputs received by the first scrolling key inputting unit so as to alter a time on the time coordinates in the waveform display area and the waveform data of the second physiological parameter corresponding to said time; and
   a following altering unit to control the first physiological parameter acquisition unit so as to alter a time on the first coordinates in the trend display graph and the measurement value of the first physiological parameter corresponding to said altered time in accordance with the altering of the time at the time coordinates in the waveform display area.

18. The apparatus according to claim 17, further comprising:
   a pathologic event data acquisition unit to acquire pathologic event data associated with time, and display a pathologic event identifier at a position corresponding to the time when said pathologic event takes place.

19. The apparatus according to claim 18, further comprising:
   a data storage unit to store the measurement values of the first physiological parameter, the waveform data of the second physiological parameter, the pathologic event data, and the corresponding time when the pathologic event takes place in a storage device, and to set the time as a primary key to build an index logic table including data and time so as to associate the data during the storing.

20. An apparatus, comprising:
   means for acquiring measurement values of a first physiological parameter associated with times at which the respective measurement values are acquired;
   means for displaying a plurality of variations in the measurement values and the corresponding times as a trend display graph in a display device's trend display area, the trend display area comprising a first coordinate and a second coordinate that represent the times and the measurement values, respectively, wherein displaying the plurality of variations in the measurement values with respect to the second coordinate in the trend display area indicates a trend in the first physiological parameter throughout a monitoring period;
   means for acquiring a selected time in the trend display area;
   means for acquiring waveform data of a second physiological parameter associated with formation of the first physiological parameter during predetermined periods before and after the selected time thereof; and
   means for displaying the waveform data in a waveform display area of the display device, the waveform display area comprising time coordinates representing waveform time.

21. A computer-readable medium comprising program code for performing a method used in an apparatus for analyzing physiological parameters, the apparatus including a physiological parameter acquisition unit and a display device, the method comprising:
   reading, using the physiological parameter acquisition unit, measurement values and corresponding times of a first physiological parameter, and displaying a plurality of variations in the measurement values over time as a trend display graph in a trend display area of the display device, the trend display area comprising first coordinates and a second coordinates that represent the times and the measurement values, respectively, wherein displaying the plurality of variations in the measurement values with respect to the second coordinate in the trend display area indicates a trend in the first physiological parameter throughout a monitoring period;

acquiring a time selected in the trend display graph; and displaying, in a waveform display area of the display device, waveform data of a second physiological parameter associated with the formation of the first physiological parameter during predetermined periods before and after the selected time, the waveform display area comprising time coordinates representing waveform time.

22. The computer-readable medium of claim 21, wherein acquiring the selected time comprises:

allowing a user to position a cursor in the trend display graph at the selected time.

23. The computer-readable medium of claim 22, the method further comprising:

receiving a coordinate position of the cursor; and displaying a time corresponding to the coordinate position of the cursor in the trend display area.

24. The computer-readable medium of claim 23, the method further comprising:

displaying indicia of the time corresponding to the coordinate position of the cursor in the waveform display area.

25. The computer-readable medium of claim 21, the method further comprising:

displaying a pathological event identifier in at least one of the trend display area and the waveform display area at a position corresponding to a time when a pathological event takes place.

26. A method used in an apparatus for waveform analysis of physiological parameters, the apparatus including a physiological parameter acquisition unit and a display device, the method comprising:

reading, using the physiological parameter acquisition unit, measurement values and corresponding times of a first physiological parameter, and displaying a plurality of variations in the measurement values of the first physiological parameter over time as a trend display graph in a trend display area of the display device, the trend display area comprising a first coordinate and a second coordinate that represent the times and the measurement values, respectively, wherein displaying the plurality of variations in the measurement values with respect to the second coordinate in the trend display area indicates a trend in the first physiological parameter throughout a monitoring period;

acquiring a time selected in the trend display graph;

displaying, in a waveform display area of the display device, waveform data of a second physiological parameter associated with the formation of the first physiological parameter during predetermined periods before and after the selected time, the waveform display area comprising time coordinates representing waveform time;

storing the measurement values of the first physiological parameter, the waveform data of the second physiological parameter, pathologic event data, and a time corresponding to when a pathologic event takes place, in a data storage device; and setting the time corresponding to when the pathologic event takes place as a primary key to build an index logic table including data and time so as to associate the data during the storing step.

27. The method according to claim 26, wherein magnitudes of the measurement values of the first physiological parameter are represented by lengths of respective lines.

28. The method according to claim 27, further comprising:

displaying an end-point gauge at an end point of the trend graph, the end-point gauge indicating an end of data corresponding to the first physiological parameter; and moving the end-point gauge dynamically as time elapses.

29. The method according to claim 26, wherein acquiring the selected time comprises:

positioning a cursor in the trend display graph at the selected time.

30. The method according to claim 29, further comprising:

receiving the coordinate position of the cursor; and displaying a time corresponding to the coordinate position of the cursor proximate to the cursor in the trend display graph.

31. The method according to claim 29, further comprising:

displaying a middle time on the time coordinates of the waveform display area, wherein the middle time is the time selected by the cursor.

32. The method according to claim 31, further comprising:

displaying a gauge in the waveform display area for measuring a magnitude of the second physiological parameter.

33. The method according to claim 31, further comprising:

receiving inputs from a scrolling key in the waveform display area when the waveform display area is in an active state;

altering a time on the time coordinates of the waveform display area and the waveform data of the second physiological parameter corresponding to the time; and altering a time on the first coordinates of the trend display graph and a measurement value of the first physiological parameter corresponding to the time in accordance with the altering of the time on the first coordinates of the waveform display area.

34. The method according to claim 33, further comprising:

displaying a pathologic event identifier at a position corresponding to the time when the pathologic event takes place.

35. The method according to claim 33, further comprising:

varying a length of the displayed waveform data of the second physiological parameter in the waveform display area according to a user-selectable wave speed, wherein the faster the wave speed, the shorter a waveform corresponding to the waveform data displayed in the waveform display area.

36. The method according to claim 26, wherein the first physiological parameter is a heart rate, and the second physiological parameter is electrocardiogram data.

* * * * *